125-675
2/24/87 OR RE 32,361

United States Patent [19]

Duggan

[11] E Patent Number: Re. 32,361

[45] Reissued Date of Patent: Feb. 24, 1987

[54] IMPLANTABLE TELEMETRY TRANSMISSION SYSTEM FOR ANALOG AND DIGITAL DATA

[75] Inventor: Stephen R. Duggan, Rosemount, Minn.

[73] Assignee: Medtronic, Inc., Minneapolis, Minn.

[21] Appl. No.: 399,638

[22] Filed: Jul. 19, 1982

Related U.S. Patent Documents

Reissue of:

[64] Patent No.: 4,281,664
Issued: Aug. 4, 1981
Appl. No.: 38,805
Filed: May 14, 1979

[51] Int. Cl.[3] ..... A61B 5/00

[52] U.S. Cl. ..... 128/696; 128/419; 128/903

[58] Field of Search ..... 128/696–697, 128/903, 70, 419 PT

[56] References Cited

U.S. PATENT DOCUMENTS

| | | | |
|---|---|---|---|
| 2,812,427 | 11/1957 | Magondeaux | 128/903 |
| 2,812,427 | 11/1957 | Magondeaux | 250/6 |
| 3,603,881 | 9/1971 | Thornton | 128/903 |
| 3,662,758 | 5/1972 | Glover | 128/419 E |
| 3,698,398 | 10/1972 | Berkovits | 128/422 |
| 3,872,455 | 3/1975 | Fuller et al. | 128/903 |
| 3,872,455 | 3/1975 | Fuller et al. | 340/189 M |
| 3,888,260 | 6/1975 | Fischell | 128/419 PG |
| 3,942,535 | 3/1976 | Schulman | 128/419 PS |
| 3,952,750 | 4/1976 | Mirowski et al. | 128/419 D |
| 3,997,848 | 12/1976 | Rippy | 329/122 |
| 4,026,305 | 5/1977 | Brownlee et al. | 128/419 PT |
| 4,041,954 | 8/1977 | Ohara | 128/419 PT |
| 4,142,533 | 3/1979 | Brownlee et al. | 128/419 PT |
| 4,172,459 | 10/1979 | Hepp | 128/697 |
| 4,223,679 | 9/1980 | Schulman et al. | 128/419 PT |
| 4,236,523 | 12/1980 | Gruenenwald | 128/419 PT |

OTHER PUBLICATIONS

"A Totally Implantable Multi—Channel Telemetry System Using Custom Integrated Circuits", Knutti, et al, pp. 63–66.

"Single Frequency RF Powering", Ko, et al, pp. 67–70.

"An Inductively Powered Implantable Multichannel Telemetry System For Cardiovascular Data", McCutcheon, et al. pp. 71–74; BIOTELEMETRY III, Academic Press, Inc., N.Y. 1976.

*Primary Examiner*—William E. Kamm

*Attorney, Agent, or Firm*—Robert C. Beck; Joseph F. Breimayer; John L. Rooney

[57] ABSTRACT

An improved telemetry transmission system for transmitting electrocardiographic information, indications of the occurrence of the pacing pulse and for transmitting digitially encoded information from an implanted pacemaker, an implanted drug dispensing device, or other implanted device, to a remote receiver. Digital data transmitted by the implanted system may include all programmed parameters as well as power source status and self test indications, or other programmed digital data such as the device serial number and lot number.

14 Claims, 4 Drawing Figures

IMPLANTABLE TELEMETRY TRANSMISSION SYSTEM FOR ANALOG AND DIGITAL DATA

Matter enclosed in heavy brackets [ ] appears in the original patent but forms no part of this reissue specification; matter printed in italics indicates the additions made by reissue.

DESCRIPTION

BACKGROUND OF THE INVENTION

The present invention relates to a telemetry system for transmitting information detected by or relating to electronic devices such as implanted cardiac pacemakers or implanted medication dispensing devices to an external receiver for recording and analysis or for retransmission over phone lines to a remote location.

Adequate evaluation of the operation of implanted electronic prosthetic devices such as pacemakers is necessary to verify their proper operation and to avoid undetected premature performance degradation so that corrective steps may be taken promptly. Although some systems have been previously described which claim to have achieved adequate monitoring of one or more variables in connection with the operation of an implanted pacemaker, those systems have proven to be cumbersome in providing usable information to an external terminal.

In addition, the prior art systems have not generally attempted to solve the problems of transmitting information from a metal encased implantable device. Prior art systems have also failed to consider the compatibility of the telemetry system with a programmable pacemaker or other remotely programmed implantable device which operates at some times in response to an externally generated programming signal.

A telemetry patent, U.S. Pat. No. 4,026,305, to Tyers, relates to a telemetry system for transmitting a signal indicating the battery voltage of a pacemaker to an external monitor. The system disclosed in Tyers is not usable for transmission of electrocardiogram information or for digital data. The Tyers system uses a low pass system which includes 60 Hz and 120 Hz.

Further, the problem of minimizing the power consumption of a two-way telemetry system capable of transmission through a metal shield has not been adequately addressed.

The present invention accordingly provides a two-way telemetry system utilizing an improved ultra-low power circuit for transmission of pacemaker EKG, analog data, or stored digital data to an external terminal. The system operates to permit monitoring of the electrical activity on the lead of an implantable pacemaker without attaching external or catheter electrodes to the patient. The receiver uses a bandpass system which operates above the common noise frequencies of 60 Hz and 120 Hz.

To receive transmitted data, a receiving coil antenna is placed over the implantable pacemaker and the pacemaker is commanded by applying a programming signal to its circuitry to cause it to send out the electrogram, the pacing pulse, or other data to the remote receiver.

The transmitting circuitry of the present invention is compatible with the antenna and receiving circuitry shown in co-pending application entitled Digital Cardiac Pacemaker, filed Nov. 6, 1978, under Ser. No. 957,958, now U.S. Pat. No. 4,230,128 naming Ray S. McDonald as the inventor. That application discloses a pacemaker pulse generator which can be remotely programmed.

BRIEF DESCRIPTION OF THE DRAWINGS

A preferred embodiment of the present invention is hereafter described with specific reference being made to the following figures in which.

BLOCK DIAGRAM OF TRANSMITTER

Figure 1:
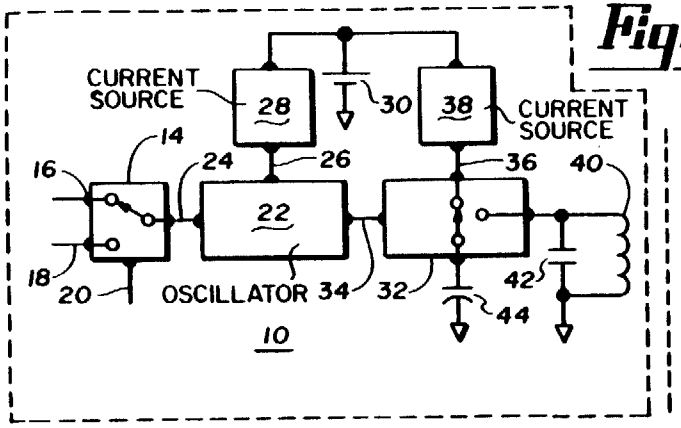
FIG. 1 is a simplified block diagram of the entire telemetry system.

Referring now to FIG. 1, there is shown a block diagram of the implantable transmitter 10 and of the receiver 12 used therewith. The dashed line 13 generally designates the skin of the patient in which the transmitter 10 is implanted. The block diagram of the transmitter 10, which is enclosed within a sealed metallic case 13 made of titanium or some similar material. A solid state switch module 14 which receives analog data at an input 16 and digitial data at an input 18 is shown within case 13. The sources of the analog and digital data provided to inputs 16 and 18 are discussed more fully below.

The analog signal may, in cardiac pacemaker applications, be derived from any of a number of sources. Through appropriate conventional switching, analog signals indicative of the endo or myoelectrogram or pacing artifact may be provided. Typical pacing artifacts are the actual pacing pulse, a voltage indicative of the charging of the pacemaker output stage capacitor or a signal indicative if lead electrode repolarization. Any low voltage 0.1 Hz to 80 Hz bandwidth analog signal lends itself to transmission utilizing the system disclosed.

Digital data suitable for transmission is required to be in non-return to zero digital pulses shifted at 10 msec per bit. In digital pacemakers such as the one disclosed in my co-pending application, continuation-in-part Ser. No. 127,308, filed Mar. 5, 1980, entitled Multimode Adaptable, Implantable Pacemaker, data relating to the operation of the device is located in a number of memory locations as 8 data bit words. Such digital data can be readily put into asynchronous non-return to zero form with a start bit, 7 or 8 data bits, a parity bit, and a stop bit. The formatting of the data can be accomplished with commercially available UART circuits such as the CDP 1854 UART sold by RCA and other manufacturers.

The digital data input terminal 18 may also be used to generate a calibrating signal for use in calibrating the EKG channel in a recorder connected to the telemetry receiver.

Solid state switch 14 acts in response to a digital-/analog control signal on terminal 20 to select either analog or digital data for transmission. Such a signal can be internally generated within a programmable digital pacemaker. The output of the solid state switch 14 is connected to the input of a voltage controlled oscillator 22 through a conductor 24. The voltage controlled oscillator 22 also receives a controlled current on conductor 26 which is regulated by a constant current source 28 driven by a voltage source 30. In the embodiment shown, the supply voltage is nominally 5 volts. Use of low threshold CMOS circuitry in the transmitter 10 would allow use of an even lower nominal voltage for the power source.

The output of the voltage controlled oscillator 22 is connected to control the operation of a further solid state switch 32 through conductor 34. Solid state switch 32 receives a controlled current through conductor 36. The controlled current is supplied by a current regulating circuit 38 which is in turn connected to voltage source 30. The output of the solid state switch 32 is connected to an antenna coil 40 across which is connected a capacitor 42.

The magnitude of the voltage at output of the solid state switch 14 linearly modulates the free running frequency of the voltage controlled oscillator or VCO 22 as a function of the input voltage. In the preferred embodiment shown, the free running frequency of VCO 22 is 1500 Hz and the modulation scale factor is 10 Hz per millivolt. The 1500 Hz free running frequency was selected to correspond to the center of the band width of a standard telephone system, and the scale factor was selected for compatibility with typical ±20 mvolt EKG signals.

The output of voltage controlled oscillator 22 on line 34 is used to control the action of the solid state switch 32. When the voltage controlled oscillator 22 has a low output voltage representative of a logic zero, switch 32 is in the position shown in FIGS. 1 and 3, and connected to receive current from the constant current source 38 and charge capacitor 44. In the specific embodiment shown, the increase of voltage across capacitor 44 during the charging cycle is typically in the vicinity of 18 millivolts. When the output of the voltage controlled oscillator 22 is a high voltage corresponding to a logic 1, the solid state switch 32 switches to the other position connecting the capacitor 44 to dump its energy into the tuned parallel combination of capacitor 42 and the antenna coil 40.

It should be pointed out that capacitor 42 tunes antenna coil 40 to the resonant frequency of input programming pulses as discussed in the above-identified Digital Cardiac Pacemaker patent application to Ray S. McDonald. Thus, the antenna coil functions not only as a transmitting antenna as described herein, but also as a receiving antenna when switch 32 is in a position to charge capacitor 44.

The tuned combination of capacitors 42 and 44 and coil 40 oscillates at a resonant frequency of 10 kHz. It is important to limit the damped sinusoid frequency F1 to approximately 10 kHz or less to minimize the attenuation of the signal by the titanium case used to enclose the antenna and circuitry. The damping factor of the equivalent parallel tuned circuit comprising capacitors 42 and 44 and conductor 40 should not exceed 0.2 to assure oscillation of the tuned circuit.

The damped sinusoidal voltage created across antenna 40 is important in the operation of the telemetry system and creates a distinct advantage in performance over systems, such as Tyers, which drive the transmitting antenna with a fixed level voltage. In the present invention, use of a damped sinusoidal voltage across antenna 40 creates an electromagnetic field whose maximum strength occurs at the frequency F1, which in the preferred embodiment occurs at a frequency of approximately 10 kHz. In contrast, a fixed voltage impressed across an antenna such as 40 would cause the maximum energy to be concentrated at zero frequency and diminish at higher frequencies in accordance with an envelope of sine F divided by F as is commonly known in the art. All things being equal, a receiver such as 12 which detects this radiated energy must be tuned to a very low frequency to recover the transmitted energy. This is undesirable since the prevalent noise frequencies of 60 Hz and 120 Hz are included in the frequencies.

In the preferred embodiment discussed, a receiver such as 12 which is receiving radiated evergy from an antenna driven with damped sinusoidal voltage would be tuned at a frequency F1 of 10 kHz to avoid reception of the noise frequencies of 60 and 120 Hz. Use of damped sinusoidal frequency modulated signals as disclosed thereby results in a desirable noise-free operation and a more cost-effective system since costly noise filters are not necessary.

Figure 2:
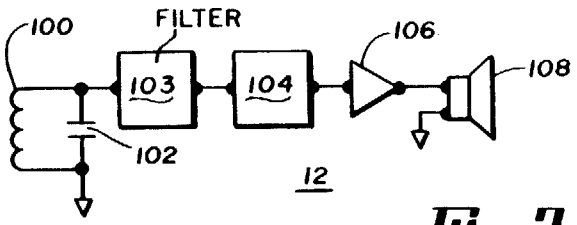
FIG. 2 shows the type of damped sinusoid signals transmitted by the system.

FIG. 2 illustrates the nature of the voltage waveform across the antenna coil 40 as a function of time. The frequency F1 is the 10 kHz resonant frequency of the antenna 40, its associated capacitor 42 and capacitor 44, while the frequency F2 represents the 1.5 kHz frequency modulated signal which appears at the output of the voltage controlled oscillator 22.

SCHEMATIC OF TRANSMITTER

Figure 3:
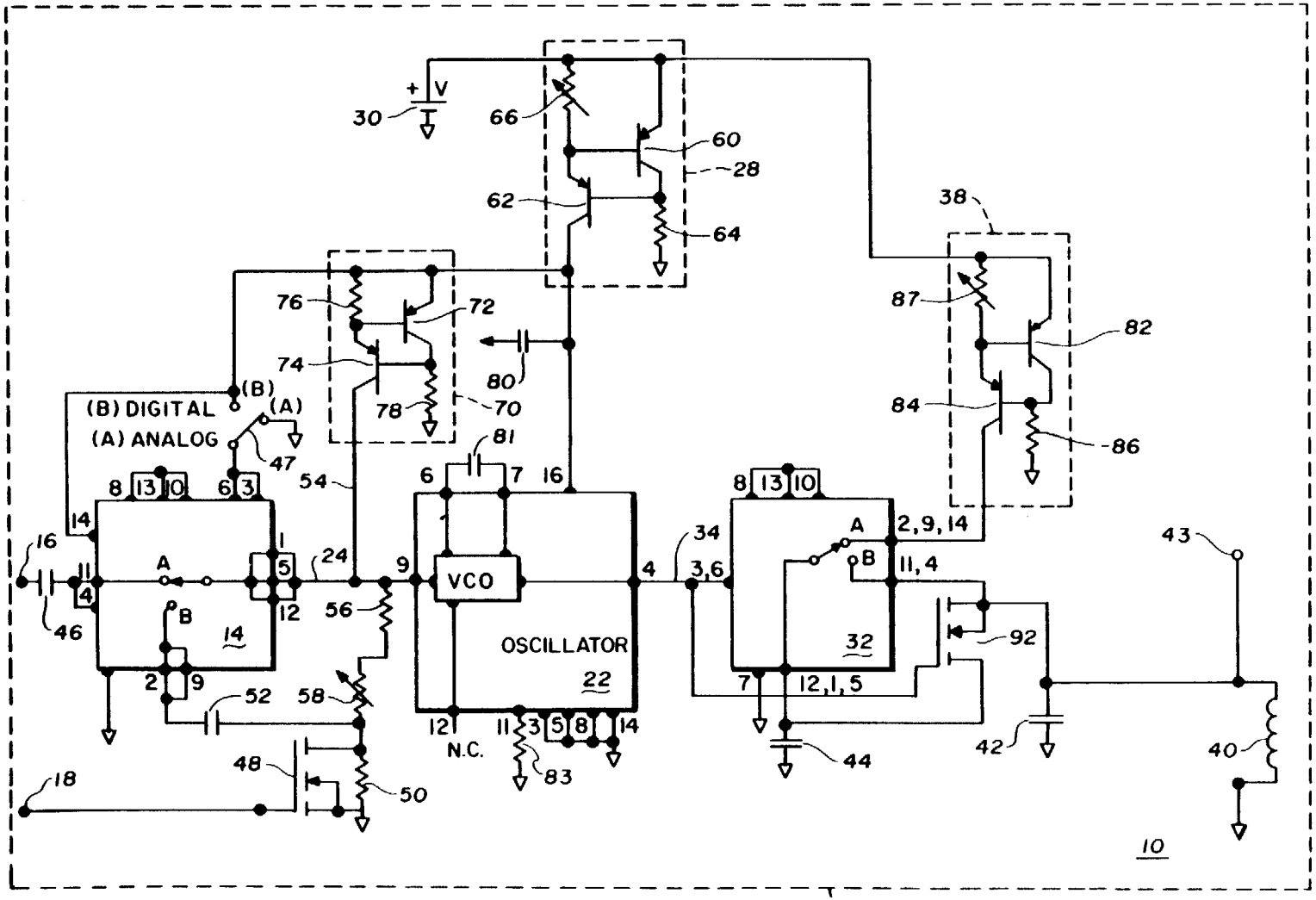
FIG. 3 is a detailed schematic diagram of the transmitter circuitry.

FIG. 3 is a detailed schematic of the transmitter circuitry 10 shown in FIG. 1 with the components which are shown in FIG. 1 similarly numbered. The analog input at terminal 16 is connected to the input terminal of solid state switch 14 through a DC blocking capacitor 46 which has a sufficiently large capacitance to provide a low frequency response sufficient to pass a 0.1 Hz sine wave and large enough to prevent distortion of an EKG signal due to differentiation.

The signal after passing through blocking capacitor 46, is connected to the input terminals of the solid state switch 14. The indicated terminal designations for solid state switches 14 and 44 and the terminals for the voltage controlled oscillator 22 are all as specified by the manufacturer. Switch 14 operates to connect either the analog input received at terminal 16 or the digital input received at terminal 18 to the input of terminal 9 of the voltage controlled oscillator 22.

Switch 47 is shown in FIG. 3 with its wiper tied to terminals 3 and 6 of switch 14, which are grounded when an analog input is selected. When a digital input signal or a calibration signal is to be received at terminal 18, switch 47 is moved to position B with terminals 3 and 6 tied to a positive voltage. Switch 47 or an associated logic signal such as 20, shown in FIG. 1, can be generated by the prosthetic device control logic to cause the transmitter to select a digital or analog input. Alternatively, switch 47 can be actuated from outside of the body in which the transmitter is implanted by using a magnetic reed switch to switch between input signals.

In the specific circuit shown in FIG. 3, the digital input port 18 is connected to an N channel transistor switch module 14. When the voltage at terminal 18 is high, the transistor 48 places a low impedance path across resistor 50, and the voltage change across resistor 50 which is caused by the switching of transistor 48, is coupled through a capacitor 52 through the solid state switch 14.

When solid state switch 14 is in position B to receive digital input data from terminal 18, a path through the switch is provided from the constant current cirucit 70 used to provide input bias to the voltage controlled oscillator 22. The bias circuit 70 provides a current of approximately 0.5 microamperes along conductor 54. Since in the preferred embodiment, bias resistors 56 and 58 have a total impedence of approximately 1.5 megohms, and resistor 50 has a resistance of approximately 20 K ohms, the switching of transistor 48 across resistor 50 does not measurably alter the input bias to the voltage controlled oscillator 22 unless the switch of the solid state switch 14 is in position B as shown to select digital data.

The ten millivolt voltage swing across resistor 50 is transmitted through capacitor 52 and switch 14 to the input of the voltage controlled oscillator 22 with a rapid rise time. The digital input can thus be used to calibrate an EKG recorder receiving the signal from the transmitter to provide an output signal indicative of a 10 mv input signal.

FIG. 3 also shows a current regulator 28 connected to the power supply 30. In the preferred embodiment shown, the current regulator comprised of PNP transistors 60 and 62 and resistors 64 and 66 is adjusted to provide a constant current of approximately 3.5 microamperes nominal from the collector of transistor 62. Variable resistor 66 is used to adjust the current delivered.

The output of current regulator 28 is delivered to the positive supply voltage terminal of the voltage controlled oscillator 22 and further to the current regulator 70 comprised of transistors 72 and 74 and resistors 76 and 78 which establish a controlled current output from the collector of transistor 74 of 0.5 microamps nominal as a bias current to the input of the voltage controlled oscillator 22. Capacitor 80 is connected to the output of the current regulator 28 to smooth the supply voltage applied to the voltage controlled oscillator 22. Capacitor 81 is connected between pins 6 and 7 of VCO 22, while resistor 83 is connected between pin 11 and ground.

The regulation and limiting of the current delivered to the voltage controlled oscillator 22 limits the current consumption of the oscillator to a value preset by the constant current source to prevent voltage controlled oscillator 22 from drawing excessive current. By limiting the current supplied to voltage controlled oscillator 22 and to the output switch 32 to an amount slightly above the minimum current at which they will operate the current drain can be minimized and held constant as the voltage 22 of the voltage source 30 decays with time. Since the minimum operating voltage at which devices can operate varies between devices, it is not practical to minimize the current drawn by the various circuits by adjusting the voltage of voltage source 30.

The output of voltage controlled oscillator 22 at pin 4 of oscillator 22 is a 50 percent duty cycle, frequency modulated 1500 Hz square wave, which is converted to a damped 10 kHz damped sinusoid by the output stage 32 of the transmitter 10 as described below.

Current source 38, which is comprised of transistors 82 and 84 and resistors 86 and 87, supplies a regulated 13 microampere charging current to a 0.22 microfarad capacitor 44 through solid state switch 32 when the switch is in position A as shown in FIG. 3. Since the switch 32 is driven from conductor 32 by the 50 percent duty cycle output of VCO 22, the average current is 6.5 microamperes nominal. The current from current regulator 38 charges capacitor 44 to approximately 18 millivolts during the half period of the 1500 Hertz drive signal from the voltage controlled oscillator output 34 when the voltage is low.

During the half period when the VCO 22 has a logic one at its output terminal 4, the switch in solid state switch 32 is in the B position, which turns the field effect transistor 92 on, providing a low impedance path for capacitor 44 to discharge the energy stored in the previous half cycle into the parallel combination of capacitor 42 and antenna 40. The action of dumping the stored charge in capacitor 44 into the parallel combination of capacitor 42 and inductor antenna 40 causes the antenna voltage to oscillate as a damped sinusoid whose frequency and amplitude are readily controlled by the selection of capacitor values 42 and 44, inductance and resistance of antenna 40 and the charging current from current source 38 according to formulae known to those skilled in the art. The capacitance of capacitor 42 and the inductance of antenna 40 are selected to resonate at a frequency of 175 K Hertz, which is the receiving frequency of the antenna of the device disclosed in the above-identified patent application for Digital Cardiac Pacemaker of Ray S. McDonald.

In the preferred embodiment shown, capacitor 42 has a capacitance of 330 picofarads, capacitor 44 has a value of 0.22 microfarads, and the inductance of the antenna 40 is approximately one millihenry. Since capacitor 44 is much larger than capacitor 42, inductor 94 and capacitor 42 resonate as they receive the stored energy in capacitor 90 as a damped sinusoid at 10 kilohertz. The frequency of the damped sinusoidal oscillation is controlled primarily by capacitor 44 and inductor 40, while the repetition rate of the pulses is determined by the VCO 22. Note also, that when a switch 32 is in position A, the solid state switch 32 and the field effect transistor 92 are connected in such a way as to isolate capacitor 44 from the parallel tuned circuit consisting of capacitor 42 and inductor 40. This design allows the inductor 40 and capacitor 42 to function as a receiving parallel tuned circuit without appreciable attenuation caused by other components in the circuit. Inductor antenna 40 therefore functions not only as a transmitting antenna, but also as a receiving antenna, which may be connected to receiving circuitry at terminal 43, thereby achieving benefits of lower cost and fewer components by having a dual function. A suitable receiving circuit is shown in the McDonald application identified above.

The transmitter 10, when not in operation, does not place a load on antenna 40 which has a significant effect on its ability to receive externally transmitted information at 175 kHz. Tests of the unit indicate that the loading of the transmitter on the antenna is less than 0.5 db when the transmitter is not active.

RECEIVER CIRCUITRY

Referring again to FIG. 1, a block diagram of the receiver section 12 is shown. The receiver consists of an antenna section 100 and a tuning capacitor 102 which are connected to a band pass filter 103 which delivers its signal to a phase lock loop circuit 104 which provides its output signal to an amplifier 106 which drives a loud speaker 108 or some other indicating means.

Figure 4:
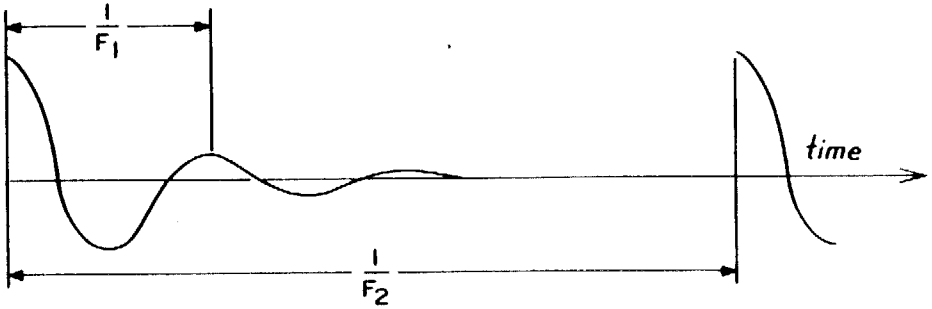
FIG. 4 is a detailed schematic of the receiving circuitry.
Figure 4:
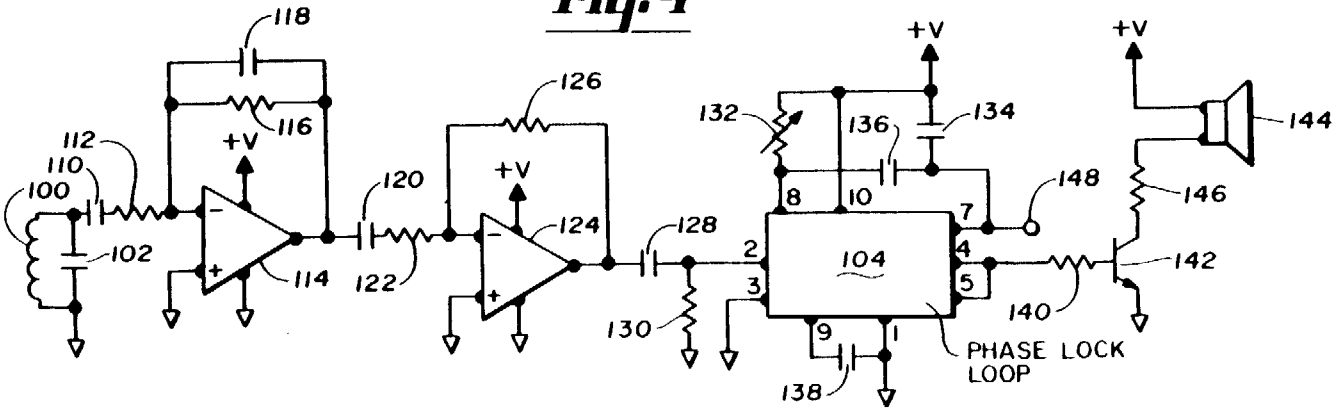

A more detailed schematic of the circuitry of the receiving section 12 is shown in FIG. 4. The antenna in a preferred embodiment is wound from 1500 turns of #30 AWG wire in a loop having a diameter of approximately 10 centimeters. The inductance of the coil is approximately 0.396 henrys, and the coil was tuned with a shunt capacitor 102 to resonate at 10 kHz.

The antenna output is connected through a coupling capacitor 110 and a resistor 112 to the input of the first stage 114 of the band pass amplifier shown in FIG. 1, as block 103. Each stage of the amplifier provides independent control of low frequency cutoff and high frequency cutoff frequencies and provides a single order or six decibels per octave attenuation beyond the respective cutoff frequencies. The low frequency break point is determined by the values of resistor 112 and capacitor 110 while the high pass break point is determined by feed back resistor 116 and capacitor 118 for the first amplifier 114. Similarly, the low frequency break point is determined by the values of resistor 122 and capacitor 120 while the high frequency break point is determined by the values of resistor 126 and its stray capacitance for amplifier stage 124.

The particular advantage of the band pass amplifier configuration shown in FIG. 4 is that the amplifier's pulse response does not produce an oscillatory output because the poles of the amplifier Bode plot are always real rather then imaginary. This characteristic of the band pass amplifier is important in the disclosed receiver, since the received information signal from the transmitter is a damped sinusoid pulse.

The output of amplifier 114 is connected through a capacitor 120 and a resistor 122 to the input of the second band pass amplifier stage 124 which has a feed back resistor 126 connected between its output and its noninverting input terminals. The output of the second stage 124 of the band pass amplifier 103 is connected through a capacitor 128 to the input terminal of the phase lock loop circuit 104 and to one end of a grounded resistor 130.

The phase lock loop circuit is connected in an FM demodulation circuit arrangement. When the input 2 to the phase lock loop circuit 104 is grounded, the output frequency at terminals 4 and 5 is 1500 Hz. The pin designations are those indicated by the manufacturer. The FM demodulator circuit and its characteristics are described in further detail in Signetic Analog Manual, dated 1976, at Page 623.

Resistor 132 is an adjustable resistor used to set the phase lock loop circuit at 1500 Hz with its input at terminal 2 grounded. The oscillator output of the phase lock loop 104 is connected to a resistor 140 which provides the base drive to a grounded emitter NPN transistor 142, which in turn, drives a loud speaker or similar transducer 144 through a resistor 146. The capture range of the VCO as configured in FIG. 4 is plus or minus 434 Hz, while the lock range is plus or minus 2 kHz. Since the transmitter 10 has a voltage controlled oscillator scale factor of 10 Hz per millivolt deviation, the receiver circuit has the ability to receive an EKG signal of plus or minus 43 millivolts.

The output stage, including transistor 142, amplifies the 1500 Hertz FM square wave at the output of the voltage controlled oscillator to drive a small transducer 144 such as a one inch speaker which can then be positioned near a conventional telephone handset to transmit the 1500 Hz frequency modulated signal to a remote EKG machine or a digital data recorder.

Speaker 144 is connected to a telephone to transmit the frequency modulated signal over telephone lines, a receiver such as the Model 9401 Teletrace R receiver manufactured by Medtronic, Inc. can be used to demodulate the signal and provide an EKG trace. Alternatively, an analog signal representation can be directly obtained from the phase lock loop circuit on terminal 148.

Digital data can be received and converted to non-return to zero pulses which may then be decoded into numerals and characters using known terminal devices.

The preferred embodiment of the telemetry system disclosed above has been found to work well with the following values or part designations.

| Resistors | Ohms |
|---|---|
| 50 | 20K |
| 56 | 1.3 M |
| 58 | 200K |
| 64, 78, 86 | 10 M |
| 66 | 100K variable in series with 75K fixed |
| 76 | 820K |
| 83, 112, 122, 130 | 100K |
| 116 | 2.2 M |
| 126 | 47 M |
| 132 | 10K variable |
| 140 | 15K |
| 146 | 100 |
| 87 | 100K variable |
| Capacitors | Microfarads |
| 42 | 0.000330 |
| 44 | 0.22 |
| 46, 80 | 1.0 |
| 102 | |
| 118 | 0.000005 |
| 110, 120 | 0.000200 |
| 52, 128 | 0.1 |
| 134 | 0.47 |
| 136 | .001 |
| 81 | 0.000170 |
| 138 | 0.047 |
| Transistors | |
| 60, 62, 72, 74, 82, and 84 | 2N3799 |
| 48 | 3N171 |
| 92 | 2N6661 |
| 142 | 2N2222 |
| Circuits | |
| switch 14 | TA 6178 RCA |
| switch 32 | CD 4007 RCA |
| voltage controlled oscillator 22 | CD 4046 RCA |
| amplifiers 114, 124 | LM 318 National |
| phase lock loop 104 | NE 565 Signetics |

Having described the invention by way of the above examples and general description, the subject matter in which exclusive rights are claimed is defined as follows:

1. In a telemetry system for transmitting data from at least one location within a living body to an external receiver, a transmitter comprising:

input means for receiving a signal from said location and providing an electrical signal representative of said data;

modulator means for receiving said electrical signal and generating an alternating signal having a frequency which differs from a predetermined nominal frequency by an amount determined by some characteristic of said electrical signal;

antenna means;

current source means;

capacitance means; and switching means controlled by the alternating signal from said modulator means to connect said capacitance means to said current source means during half of the period of said alternating signal from said modulator means, and to connect said capacitance means to said antenna means during the other half of said alternating signal.

2. The invention of claim 1 wherein said antenna means is tuned to radiate damped sinusoidal signals having a frequency of approximately 10 kHz when said switching means connects to said capacitance means to said antenna means.

3. The invention of claim 1 wherein said antenna means has a resonant frequency of 175 kHz, the resonant frequency of said antenna means being reduced by the connection of said capacitance means to 10 kHz.

4. The invention of claim 1 wherein the predetermined nominal frequency of the output of said modulator means is approximately 1500 Hz.

5. The invention of claim 1 wherein said modulator means comprises a voltage controlled oscillator having a minimum current at which it may be operated and further comprising current limiting means for limiting the current delivered to power said voltage controlled oscillator to an amount slightly exceeding the minimum current at which said voltage controlled oscillator may be operated.

6. In the telemetry system of claim 1, a receiver comprising:

receiving antenna means;

band pass filter means connected to said receiving antenna means to receive a signal from said receiving antenna means and said filter delivering an output signal representative of received signals within the pass band; and a phase lock loop circuit connected to said band pass filter to receive the output therefrom and said circuit producing a demodulated analog output signal representative of said data.

7. A telemetry system for transmitting data from at least one location within a living body to an external receiver, a transmitter comprising:

input means for receiving a signal from said location and providing an electrical signal representative of said data;

modulator means for receiving said electrical signal and generating an alternating signal having a frequency which differs from a predetermined nominal frequency by an amount determined by some characteristic of said electrical signal;

transmitting antenna means;

current source means;

capacitance means; and switching means controlled by the alternating signal from said modulator means to connect said capacitance means to said current source means during half of the period of said alternating signal from said modulator means, and to connect said capacitance means to said transmitting antenna means during the other half of said alternating signal, said transmitting antenna means radiating a signal during said other half of said alternating signal;

a receiver comprising:

receiving antenna means adapted to receive a signal radiated by said transmitting antenna means;

band pass filter means connected to said receiving antenna means to receive a signal from said receiving antenna and said filter delivering an output signal representative of received signals within the pass band; and a phase lock loop circuit connected to said band pass filter to receive the output therefrom and said circuit producing a demodulated analog output signal representative of said data.

*8. A transmitter for transmitting signals from an implantable medical device which are representative of either analog or digital values comprising a signal controlled variable frequency oscillator means having a control terminal, signal application means for selectively presenting information signals representative of said digital and analog values to said control terminal to vary the frequency of said oscillator means in response thereto relative to a nominal output frequency of said oscillator means that exists when said information signals are not being supplied, tank circuit and antenna means having a predetermined ringing frequency of oscillation when pulsed with energy, and drive circuit means coupled to said oscillator means and to said tank circuit and antenna means for supplying pulses of energy to said tank circuit and antenna means at a rate that is proportional to the output frequency of said oscillator means whereupon said pulses are radiated from said tank circuit and antenna means as damped ringing signals wherein said drive circuit means comprises a storage capacitor and discharge means for discharging said capacitor into said tank circuit and antenna means at a rate proportional to the frequency of said oscillator means so as to cause bursts of energy to be expended in said tank circuit and antenna means and transmitted thereby.*

*9. A transmitter as claimed in claim 8 wherein said discharge means comprises switching means for controlling the charging and discharging rate of said storage capacitor under the control of the output of said oscillator means.*

*10. A transmitter as claimed in claim 9 wherein the frequency of said tank circuit and antenna means is higher than said nominal frequency of oscillation of said signal-controlled oscillator means.*

*11. A transmitter as claimed in claim 10 wherein said tank circuit and antenna means comprises inductance means and capacitance means connected in parallel and said inductance means comprises a radiation coil.*

*12. A transmitter as claimed in claim 8 wherein said discharge means comprises switching means for controlling the supply of energy pulses to said tank circuit and antenna means under the control of the output of said signal-controlled oscillator means.*

*13. A transmitter as claimed in claim 12 wherein said tank circuit and antenna means comprises inductance means and capacitance means connected in parallel and said inductance means comprises a radiation coil.*

*14. A transmitter as claimed in claim 12 wherein the frequency of said tank circuit and antenna means is higher than said nominal frequency of oscillation of said signal-controlled oscillator means.*

* * * * *